(12) United States Patent
Brewer et al.

(10) Patent No.: US 7,613,513 B1
(45) Date of Patent: Nov. 3, 2009

(54) SYSTEM AND METHOD FOR DETERMINING CARDIAC GEOMETRY

(75) Inventors: James E. Brewer, Sebaka, MN (US); Mark W. Kroll, Crystal Bay, MN (US)

(73) Assignee: Pacesetter, Inc., Sylmar, CA (US)

( * ) Notice: Subject to any disclaimer, the term of this patent is extended or adjusted under 35 U.S.C. 154(b) by 752 days.

(21) Appl. No.: 10/612,770

(22) Filed: Jul. 1, 2003

(51) Int. Cl.
*A61N 1/362* (2006.01)
(52) U.S. Cl. .................. 607/17; 607/115; 607/119; 607/123
(58) Field of Classification Search ............... 607/17, 607/27
See application file for complete search history.

(56) References Cited

U.S. PATENT DOCUMENTS

| | | | | |
|---|---|---|---|---|
| 4,173,230 A | * | 11/1979 | Digby | 607/9 |
| 4,712,555 A | | 12/1987 | Thornander et al. | 128/419 |
| 4,788,980 A | | 12/1988 | Mann et al. | 128/419 |
| 4,940,052 A | | 7/1990 | Mann et al. | 128/419 |
| 4,944,298 A | | 7/1990 | Sholder | 128/419 PG |
| 5,024,222 A | * | 6/1991 | Thacker | 607/22 |
| 5,178,149 A | | 1/1993 | Imburgia et al. | 128/662.06 |
| 5,417,715 A | | 5/1995 | Noren et al. | 607/9 |
| 5,476,483 A | | 12/1995 | Bornzin et al. | 607/17 |
| 5,662,108 A | * | 9/1997 | Budd et al. | 600/374 |
| 5,738,096 A | | 4/1998 | Ben-Haim | 128/653.1 |
| 6,009,349 A | | 12/1999 | Mouchawar et al. | 607/6 |
| 6,066,094 A | | 5/2000 | Ben-Haim | 600/437 |
| 6,077,236 A | | 6/2000 | Cunningham | 600/587 |
| 6,129,744 A | | 10/2000 | Boute | 607/25 |
| 6,195,584 B1 | * | 2/2001 | Hill et al. | 607/28 |
| 6,278,894 B1 | | 8/2001 | Salo et al. | 600/547 |
| 6,285,898 B1 | | 9/2001 | Ben-Haim | 600/374 |
| 6,336,903 B1 | | 1/2002 | Bardy | 600/508 |
| 6,421,565 B1 | | 7/2002 | Hemmingsson | 607/17 |
| 6,438,408 B1 | * | 8/2002 | Mulligan et al. | 600/510 |
| 6,445,952 B1 | * | 9/2002 | Manrodt et al. | 607/28 |
| 6,738,669 B1 | * | 5/2004 | Sloman et al. | 607/28 |
| 6,892,091 B1 | * | 5/2005 | Ben-Haim et al. | 600/509 |
| 6,976,967 B2 | * | 12/2005 | Dahl et al. | 600/508 |
| 7,003,348 B1 | * | 2/2006 | Brewer et al. | 607/17 |
| 2002/0002389 A1 | | 1/2002 | Bradley et al. | 607/8 |
| 2002/0087089 A1 | | 7/2002 | Ben-Haim | 600/509 |
| 2002/0115939 A1 | | 8/2002 | Mulligan et al. | 600/510 |
| 2003/0204212 A1 | * | 10/2003 | Burnes et al. | 607/17 |
| 2005/0027323 A1 | * | 2/2005 | Mulligan et al. | 607/18 |

FOREIGN PATENT DOCUMENTS

| | | |
|---|---|---|
| WO | WO 99/07285 | 2/1999 |
| WO | WO 01/87410 A2 | 11/2001 |
| WO | WO 01/87410 A3 | 11/2001 |
| WO | WO 02/053228 | 7/2002 |

* cited by examiner

*Primary Examiner*—Carl H Layno
*Assistant Examiner*—Brian T. Gedeon

(57) ABSTRACT

An exemplary method includes delivering an electrical signal to a first position in or adjacent to a cardiac chamber; sensing a potential generated by the delivered electrical signal at a second position; and determining a parameter based, at least in part, on the sensing wherein the parameter relates to cardiac geometry. Other exemplary methods, devices and/or systems are also disclosed.

22 Claims, 11 Drawing Sheets

EXEMPLARY METHOD

SYSTEM AND METHOD FOR DETERMINING CARDIAC GEOMETRY

CROSS REFERENCE TO RELATED APPLICATIONS

The present application is related to U.S. patent application Ser. No. 10/612,611, now U.S. Pat. No. 7,003,348, filed concurrently herewith, titled "Monitoring Cardiac Geometry for Diagnostics and Therapy," which is incorporated herein by reference.

TECHNICAL FIELD

The present invention generally relates to devices, systems and/or methods for providing cardiac pacing therapy. More particularly, various exemplary methods determine one or more parameters related to cardiac geometry.

BACKGROUND

Congestive heart failure (CHF) is a condition that is often associated with a weakened heart that cannot pump enough blood to body organs. For example, as pumping action is lost, blood may back up into the heart and other areas of the body, including the liver, gastrointestinal tract, extremities and/or lungs. While implantable cardiac therapy devices are often used to overcome deleterious effects caused by CHF, such devices cannot halt progress of CHF. However, some implantable cardiac devices can be programmed to compensate for worsening stages of CHF. For example, as CHF progresses, the myocardium weakens, which typically results in an increased left ventricular volume. To compensate for the increase in volume, a clinician may periodically measure a patient's left ventricular diameter, or another parameter associated with cardiac geometry, and program the implanted cardiac therapy device accordingly. This technique, however, requires clinical intervention, which consumes time and resources. Reliable exemplary devices, methods and/or systems for determining cardiac geometry using an implanted cardiac therapy device optionally overcome such limitations and are presented herein.

SUMMARY

An exemplary method includes delivering an electrical signal to a first position in or adjacent to a cardiac chamber; sensing a potential generated by the delivered electrical signal at a second position; and determining a parameter based, at least in part, on the sensing wherein the parameter relates to cardiac geometry. Other exemplary methods, devices and/or systems are also disclosed.

The various exemplary methods, devices and/or systems described herein, and equivalents thereof (e.g., structural and/or functional), are suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims.

Exemplary Stimulation Device

The techniques described below are intended to be implemented in connection with any stimulation device that is configured or configurable to stimulate or shock a patient's tissue (e.g., cardiac, nerve, muscle, etc.).

Figure 1:
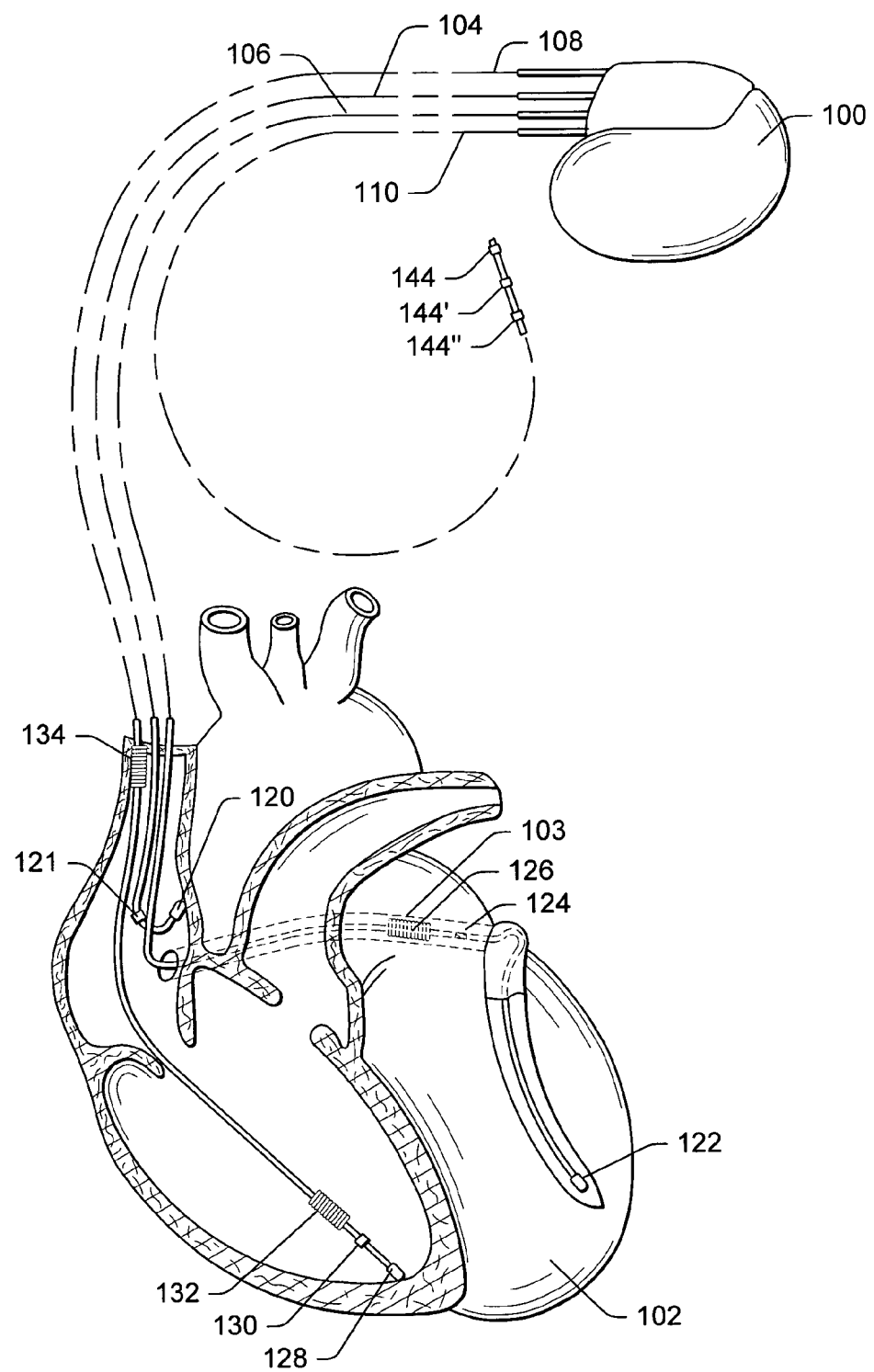
FIG. 1 is a simplified diagram illustrating an implantable stimulation device in electrical communication with at least three leads implanted into a patient's heart for delivering multi-chamber stimulation and shock therapy.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of tissue (e.g., cardiac, nerve, muscle, etc.). The exemplary lead 110 may be positioned, for example, in and/or near a patient's heart or near an autonomic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulating autonomic nerves and/or anchoring at least a portion of the lead 104.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. patent application Ser. No. 09/457, 277, filed Dec. 8, 1999, entitled "A Self-Anchoring, Steerable Coronary Sinus Lead" (Pianca et al.); and U.S. Pat. No. 5,466, 254, "Coronary Sinus Lead with Atrial Sensing Capability" (Helland), which are incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve and/or anchoring the lead, such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve and/or anchoring the lead, such an electrode may be positioned on the lead or a bifurcation or leg of the lead.

Figure 2:
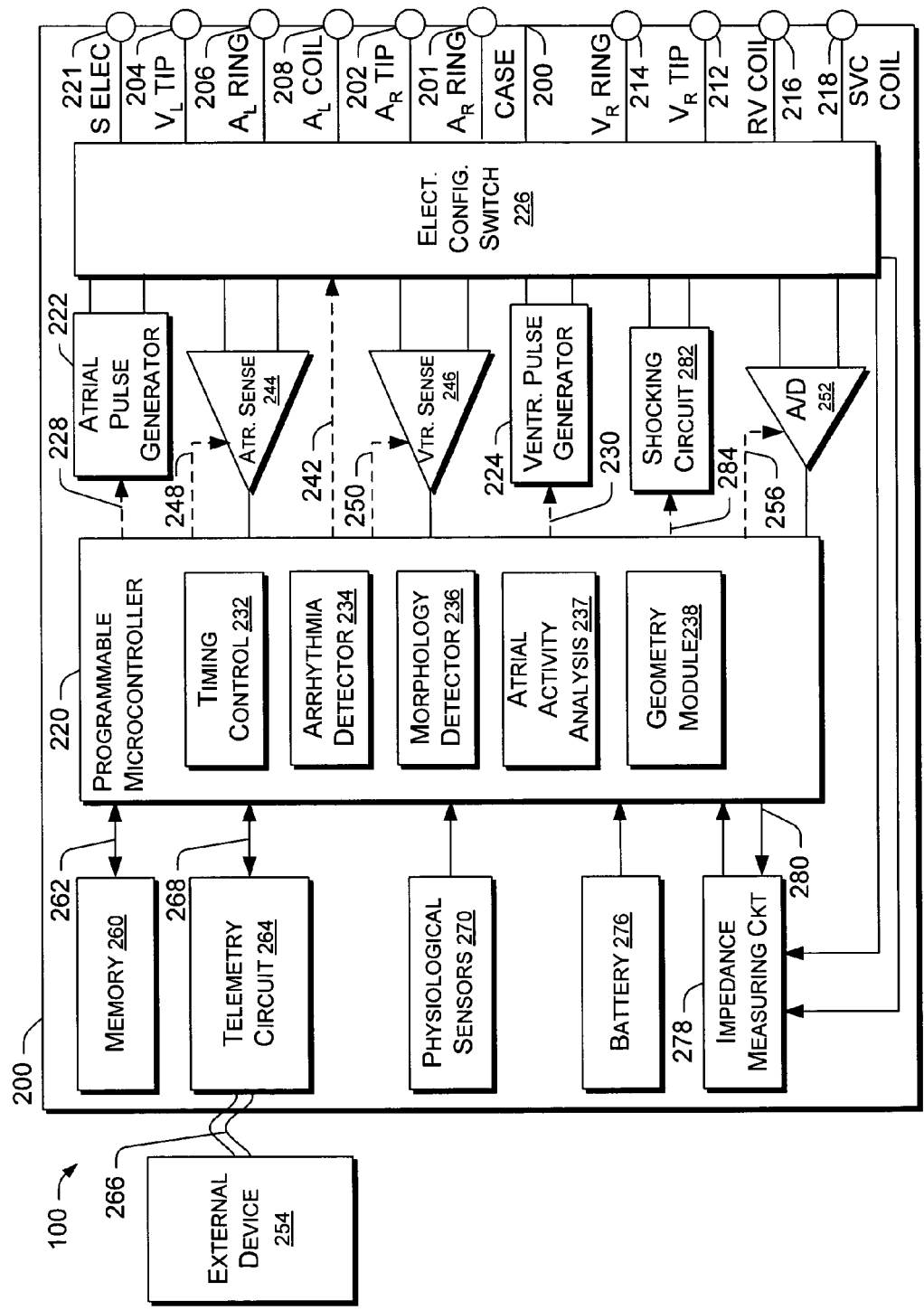
FIG. 2 is a functional block diagram of a multi-chamber implantable stimulation device illustrating basic elements that are configured to provide cardioversion, defibrillation, and pacing stimulation to the heart and/or other tissues stimulation in various places in a patient's body.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal ($A_R$ TIP) 202 adapted for connection to the atrial tip electrode 120. To achieve left chamber sensing, pacing, and shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively.

To support right chamber sensing, pacing, and shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 optionally includes a geometry module 238 for performing a variety of tasks related to use of an exemplary methods, as described in more detail below. This component can be utilized by the stimulation device 100 for aiding in implantation or positioning, electrode selection (configuration, polarity, etc.), and administration of various therapies, including tissue stimulation to effect the myocardium and/or other tissue and/or nerves. The geometry module 238 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram (IEGM) signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors to help detect movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected. Accordingly, the device 100 preferably employs lithium The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Figure 3:
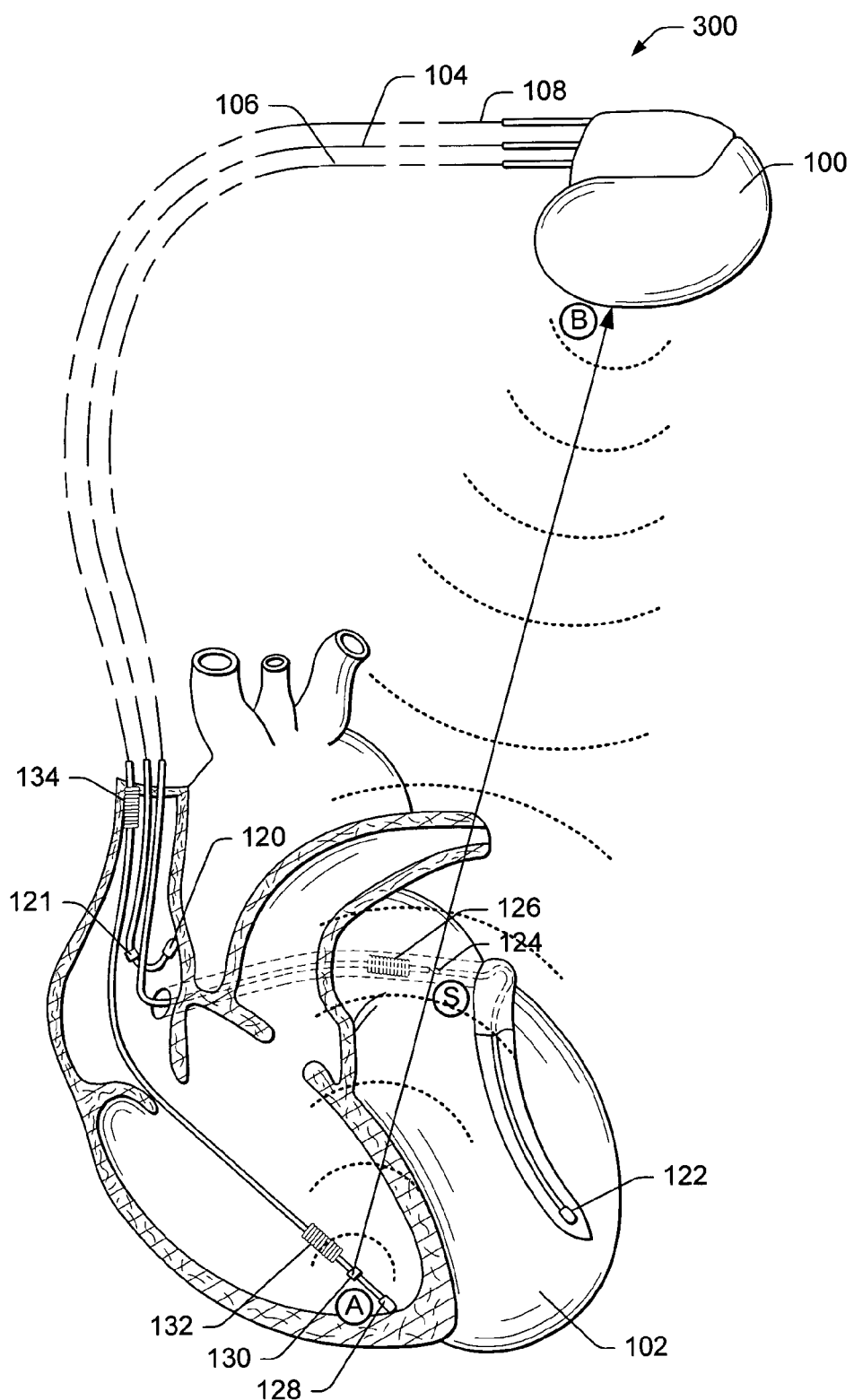
FIG. 3 is a simplified diagram illustrating an implantable stimulation device in electrical communication with leads implanted into a patient's heart for delivering signals and/or sensing.

FIG. 3 shows an exemplary signal delivery and sensing arrangement 300 having features such as those shown in FIG. 1. The exemplary device 100 has a can or case electrode, which is programmably selected to act as the return electrode for two unipolar configurations. A first unipolar configuration includes the ring electrode 130 of the right ventricular lead 108 and the case electrode of the device 100. A second unipolar configuration includes the ring electrode 124 of the left ventricular lead 106 and the case electrode of the device 100.

According to this exemplary arrangement 300, an electrical signal, delivered by a unipolar delivery circuit generates a potential field between the ring electrode 130 and the case electrode of the device 100. The potential field includes the ring electrode 124, which forms a unipolar sense circuit that includes the case electrode of the device 100. The unipolar sense circuit can sense a potential in the potential field at a point corresponding to the ring electrode 124.

The exemplary arrangement 300 may be supported by the following theory. First consider a single electrode placed in an electrically homogenous medium (e.g., having resistivity $\rho$)

and having a current I measured in amperes. The potential, U, measured in volts, at any point in the medium is given as:

$$U = \rho \frac{I}{2\pi r} \quad (1)$$

where r is the distance from the electrode. For a pair of electrodes (e.g., the can electrode of the device 100 and the ring electrode 130) having current I at electrode A and current −I at electrode B, the potential U is given by the algebraic sum of the individual contributions:

$$U = \rho \frac{I}{2\pi r_A} - \rho \frac{I}{2\pi r_B} = \frac{\rho I}{2\pi} \left[ \frac{1}{r_A} - \frac{1}{r_B} \right] \quad (2)$$

where $r_A$ and $r_B$ are the distances from the point to the electrode A and the electrode B, respectively. Of course, potentials may be sensed at more than one point by more than one electrode or a potential may be sensed in a bipolar manner between two sensing electrode. In the latter case, the potential could be approximated by $U=U_1-U_2$ (3). Equation 3 is an approximation that typically becomes more accurate for an increasingly large medium where nonlinear effects near an electrode or electrodes are minimal.

Figure 4:
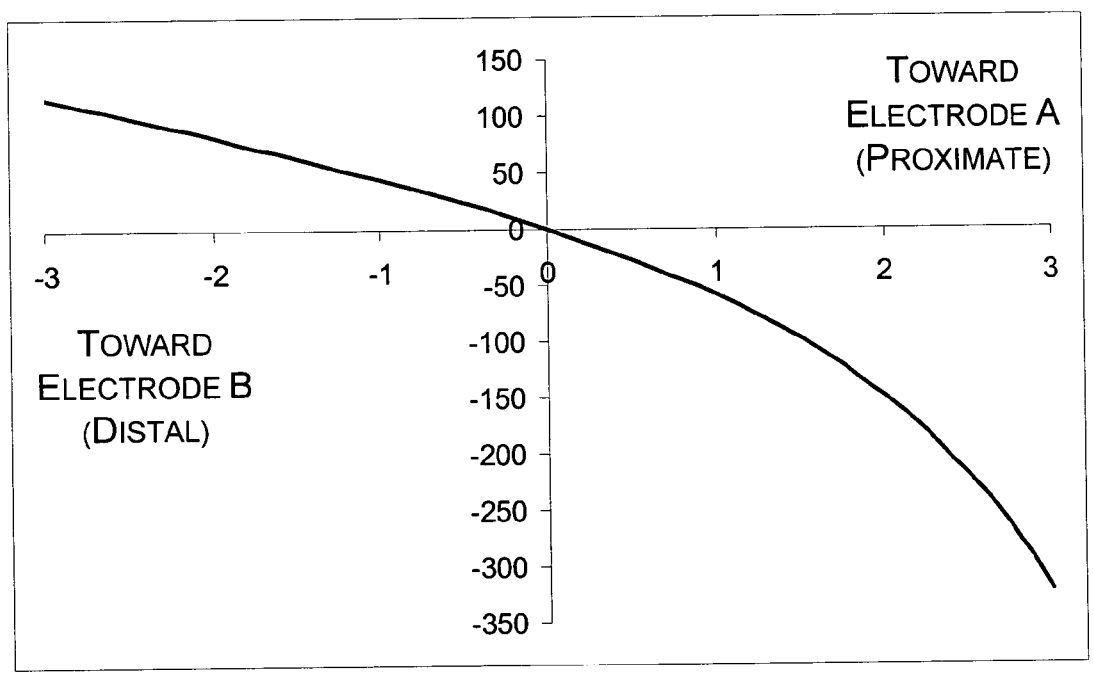
FIG. 4 is a plot of displacement versus percentage change in potential.

FIG. 4 shows an exemplary plot 400 of displacement versus percentage change in potential using Equation 2. The plot corresponds to a hypothetical scenario wherein the distance between electrodes A and B is approximately 15 cm and the distance between a sense electrode and electrode B (e.g., case or other electrode) is approximately 10 cm and the distance between the sense electrode and electrode A (e.g., ring, tip or other electrode) is approximately 5 cm. According to Equation 2, a displacement of 2.5 cm of the sense electrode along a line toward electrode B results in approximately a 100% change in the potential sensed by the sense electrode (e.g., −0.1*C to 0*C, where C is a constant) whereas a displacement of 2 cm of the sense electrode along a line toward electrode A results in approximately a 150% change in the potential sensed by the sense electrode (e.g., −0.1*C to −0.25*C, where C is a constant). Of course, if the displacement occurred along an equipotential line, then no change in potential would be expected. In general, exemplary arrangements avoid positioning of a sense electrode where displacement would occur along an equipotential line.

Note that Equation 2 relies on a resistivity ρ that corresponds to an electrically homogenous medium; a discussion of various exemplary techniques that pertain to non-homogenous media and impedance appears further below. Further note that use Equation 2 for displacement measurements in relationship to percentage change, etc., in potential does not require knowledge of resistivity ρ, see Equation 4

$$\%U = 100*(U_1 - U_2)/U_1 = 100* \left[ 1 - \left[ \frac{1}{r_{A2}} - \frac{1}{r_{B2}} \right] * \left[ \frac{1}{r_{A1}} - \frac{1}{r_{B1}} \right]^{-1} \right] \quad (4)$$

A geometry determination (e.g., a position, a displacement, etc.) may rely simply on a sensed potential which is correlated with a geometric parameter. For example, as explained in more detail below, the exemplary arrangement 300 is capable of delivering an electrical signal, sensing a potential, and determining a distance based on the sensed potential. In general, the arrangement 300 is capable of sensing a potential that is related to the physical distance between the case electrode of the device 100 and/or the ring electrode 130 and the ring electrode 124. In addition, the arrangement 300 is capable of sensing a potential that is related to the physical displacement of the ring electrode 124 or one of the other electrodes (e.g., the ring electrode 130).

Figure 5:
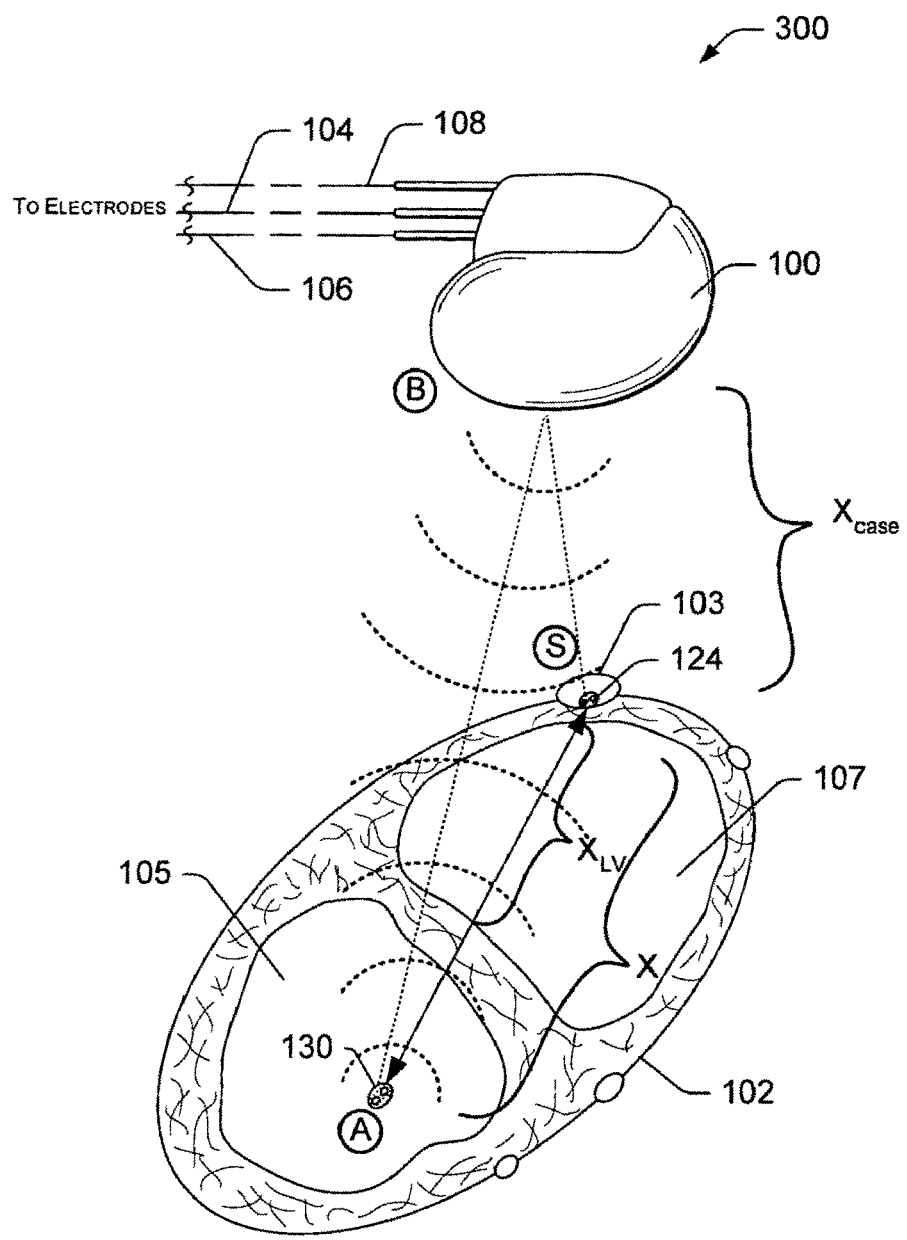
FIG. 5 is a simplified diagram illustrating an implantable stimulation device in electrical communication with leads implanted into a patient's heart for delivering signals and/or sensing wherein the heart is shown in cross-section.

FIG. 5 shows another view of the exemplary arrangement 300. In this cross-sectional view of the heart 102, the right ventricle 105 and the left ventricle 107 are visible. The ring electrode 130 is located in the right ventricle 105 while the ring electrode 124 is located in the coronary sinus 103, posterior to the left ventricle 107. As shown, "x" represents a point-to-point distance between the ring electrode 130 in the right ventricle 105 and the ring electrode 124 in the left ventricle 107 and "$x_{LV}$" represents an approximate distance across the left ventricle 107.

Figure 6:
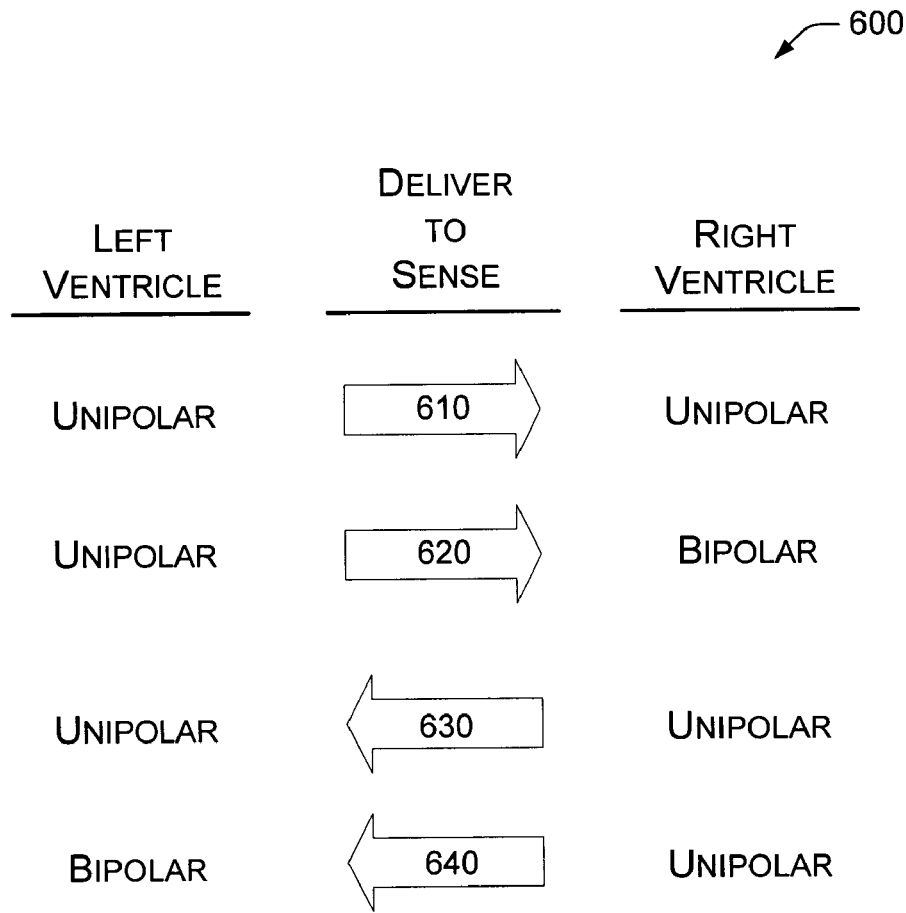
FIG. 6 is a diagram of various exemplary electrode configurations for delivering signals and/or sensing.

While the exemplary arrangement 300 includes a unipolar delivery circuit and a unipolar sense circuit, other configurations are also possible. For example, FIG. 6 shows a variety of possible exemplary delivery and sense configurations 600 (e.g., 610, 620, 630, 640). In these exemplary configurations 600, the delivery circuit generates a potential field and the sense circuit senses a potential in the field. Exemplary configuration 610 includes a left ventricular unipolar delivery circuit and a right ventricular unipolar sense circuit; exemplary configuration 620 includes a left ventricular unipolar delivery circuit and a right ventricular bipolar sense circuit; exemplary configuration 630 includes a right ventricular unipolar delivery circuit and a left ventricular unipolar sense circuit; and exemplary configuration 640 includes a right ventricular unipolar delivery circuit and a left ventricular bipolar sense circuit.

In more specific examples, in the exemplary configuration 610 the test current is delivered between the LV tip and the can while the voltage is sensed between the RV tip (or ring) and the can; in the exemplary configuration 620 the test current is delivered between the LV tip and the can while the voltage is sensed between the RV tip and ring; in the exemplary configuration 630 the test current is delivered between the RV tip and the can while the voltage is sensed between the LV tip (or ring) and the can; and, in the exemplary configuration 640 the test current is delivered between the RV tip and the can while the voltage is sensed between the LV tip and ring.

Figure 7:
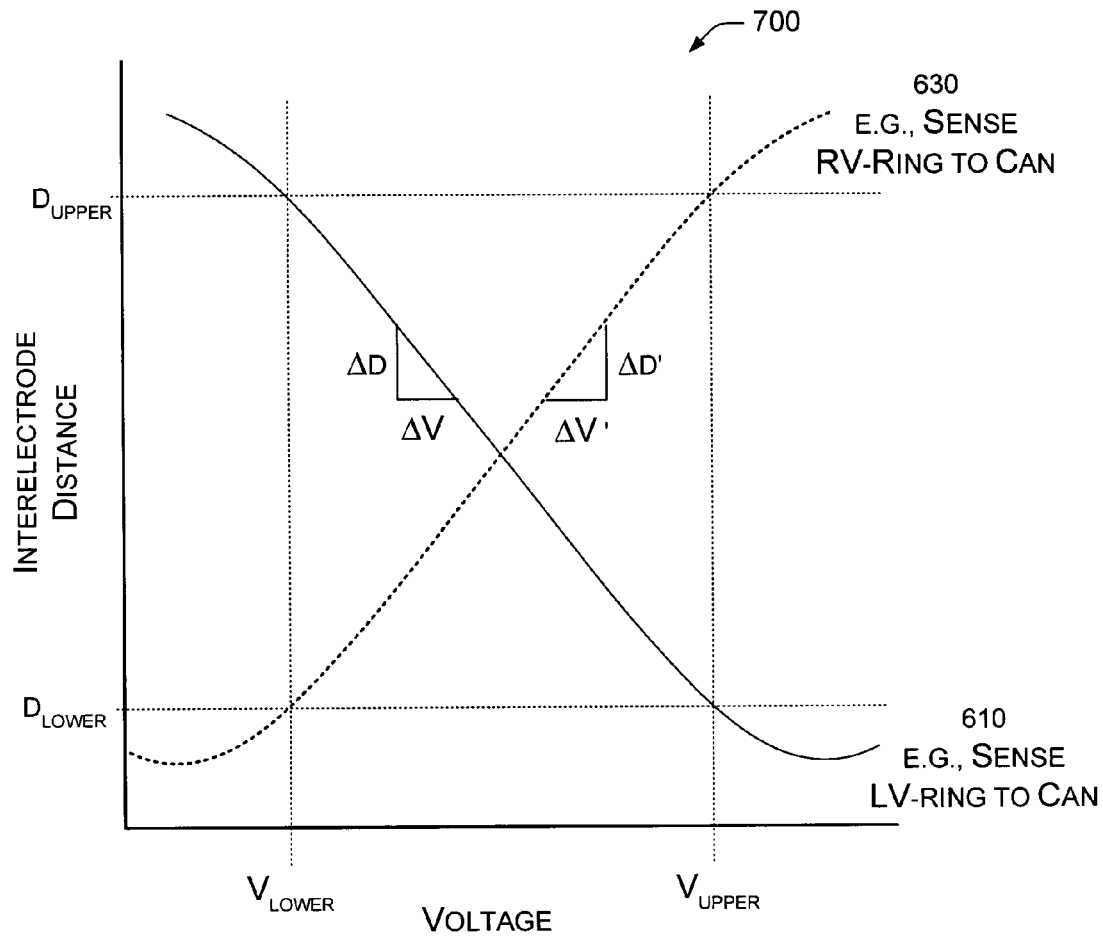
FIG. 7 is a plot of a geometric parameter versus a sensed value wherein a substantially linear relationship exists for at least a portion of the plot.

FIG. 7 shows an exemplary plot 700 of distance versus potential (e.g., voltage). The plot 700 includes a LV-ring to can sense curve 610 and a RV-ring to can sense curve 630. The LV-ring to can sense curve 610 represents potentials sensed in a potential field generated by a RV-ring to can delivery signal while the RV-ring to can sense curve 530 represents potentials sensed in a potential field generated by a LV-ring to can delivery signal. For example, delivery of a signal to the RV-ring (e.g., unipolar) at a potential of 630 mV RMS and a frequency of 1 kHz resulted in a sensed potential of approximately 0 mV to approximately 10 mV, which was substantially proportional to distance between the ring electrodes, which ranged from approximately 0 cm to approximately 15 cm. FIG. 7 indicates two substantially linear portions of the curves wherein the relationship between distance and potential fits a linear model. In the above example, a substantially linear portion for distance versus potential extended between approximately 4 cm and approximately 10 cm. This range corresponds well with dimensions of interest in the human heart. Of course, nonlinear models may extend the fit to a broader range of potentials and distances and/or improve the fit. In addition, conventional leads and electrodes may be used, or adapted for use, to determine geometric parameters for other regions of the body, which may have distance ranges less than and/or greater than those associated with the heart.

Figure 8:
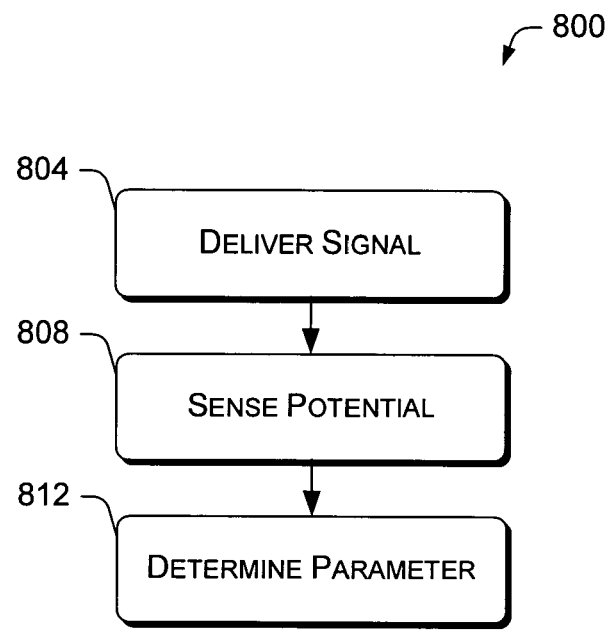
FIG. 8 is a block diagram of an exemplary method for determining a geometric parameter.

FIG. 8 shows an exemplary method 800 for determining a geometric parameter. According to the method 800, a delivery block 804 delivers an electrical signal to generate a potential field. At the same time, or shortly thereafter, a sense block 808 senses a potential in the potential field. A determination block 812 follows that determines a geometric parameter based, at least in part, on the potential.

Figure 9:
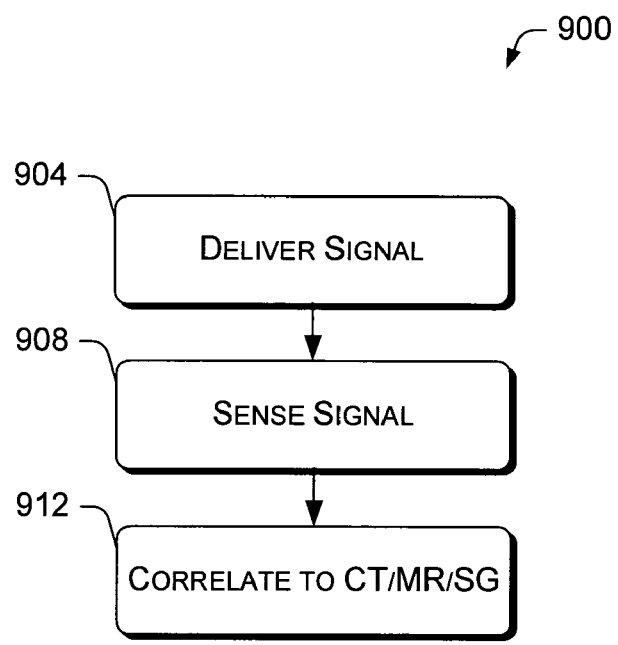
FIG. 9 is a block diagram of an exemplary method for determining a relationship between a sensed value and a geometric parameter.

FIG. 9 shows an exemplary method 900 for correlating sensed potentials with physiologic geometry (e.g., coordinates, distances, volumes, etc.). According to the method 900, a delivery block 904 delivers an electrical signal to generate a potential field. At the same time, or shortly thereafter, a sense block 908 senses a potential in the potential field. A correlation block 912 follows that correlates one or more sensed potentials to geometric information obtained via a medical imaging device, such as, but not limited to, x-ray, CT, MR, sound-based imaging, etc. The correlation is optionally saved in an implantable cardiac therapy device (e.g., as a model, database, etc.).

Impedance Measurement/Compensation

As mentioned above, Equation 2 relies on a resistivity ρ associated with an electrically homogenous medium. Depending on the circumstances, such an assumption may suffice. For example, changes in an average resistivity with respect to time may have an insignificant effect on sensed potential when compared to changes that occur in sensed potential with respect to displacement. Referring to FIG. 4, note that a 2 cm change in displacement of the sense electrode along a line toward electrode B (e.g., an electrode positioned at a distance from a pacing device) resulted in approximately a −150% increase in potential. This is due to the relationship between the variables $r_A$ and $r_B$ of Equation 2 and the potential. In contrast, according to Equation 2, the resistivity ρ would have to change by 150% to have a similar effect on the potential. Thus, in some circumstances, changes in resistivity ρ may have little effect on the sensed potential. In addition, for a potential measurement that includes a device case as part of a sensing circuit, the effect of changes in a chamber's blood volume may have an insignificant effect on an average resistivity ρ.

For circumstances that warrant knowledge of impedance for compensation or correction of distance or displacement or for determining other useful information, an exemplary device and/or an exemplary method may rely on direct and/or indirect impedance measurement. In general, resistivity ρ of a heterogenous medium will depend on resistivities of component media and amount of and/or orientation of component media. Regarding cardiac impedance (e.g., between opposing walls of a chamber), an average resistivity may depend on myocardial resistivity, blood resistivity, blood area/volume and orientation, and myocardial area/volume and orientation. Blood area/volume certainly varies with respect to time and, where warranted, impedance techniques that can estimate blood area/volume may be used to complement distance and/or displacement measurements.

Impedance is typically defined as total passive opposition offered to the flow of electric current. Biological impedance may have a relatively constant component and a time variant component. For example, cardiac output (CO) has been related to a constant impedance component, $Z_0$, and a time variant impedance component, $Z(t)$, the latter of which may be given as:

$$Z(t) = T\frac{dZ}{dt} \qquad (5)$$

where Z is impedance in ohm and T is a systolic or left ventricular ejection time in seconds. Sometimes Z(t) is given as the sum of $Z_o$ plus a time varying component. Stroke volume (SV, in ml) may be estimated as follows:

$$SV = \rho_B * (L^2/Z_0^2) * T\frac{dZ}{dt} \qquad (6)$$

where $\rho_B$ is the resistivity of the blood in ohm*cm and L is the distance in cm between two electrodes. Cardiac output (CO) may then be calculated as stroke volume (SV) multiplied by heart rate (HR).

Another impedance technique known as impedance plethysmography can estimate a chamber volume. According to this technique, impedance of blood is related to a chamber volume. To perform this technique, a lead having at least two electrodes is inserted into a chamber of the heart. Electrical resistance of a conductor is given as:

$$R = \frac{\rho L}{A} \qquad (7)$$

where R is resistance in ohms, ρ is resistivity of the conductor in ohm*cm, L is the distance between two electrodes in cm and A is the cross-sectional area of the conductor in $cm^2$. A current I is applied to the two electrodes and a potential U is measured in volts between the two electrodes. A resistance R is calculated by dividing potential U by current I. Resistivity ρ of blood is known a priori, which allows a determination of A, the cross-sectional area of the conductive blood. A series of electrodes on a lead may be used to determine a series of cross-sectional areas $A_i$ for a series of distances $L_i$. Individual volumes $V_i$ (e.g., i=1 to n) may be determined by multiplying $A_i$ and $L_i$ and a total volume $V_T$ by summing the individual volumes $V_i$.

In general, contraction of a ventricle results in a decrease in ventricular cross-sectional area (e.g., A); thus, per Equation 7, where blood is the main conductor, a ventricular contraction corresponds to an increase in resistance, which results in an increase in potential for a given current I, assuming L, the distance between two measuring electrodes remains constant.

Figure 10:
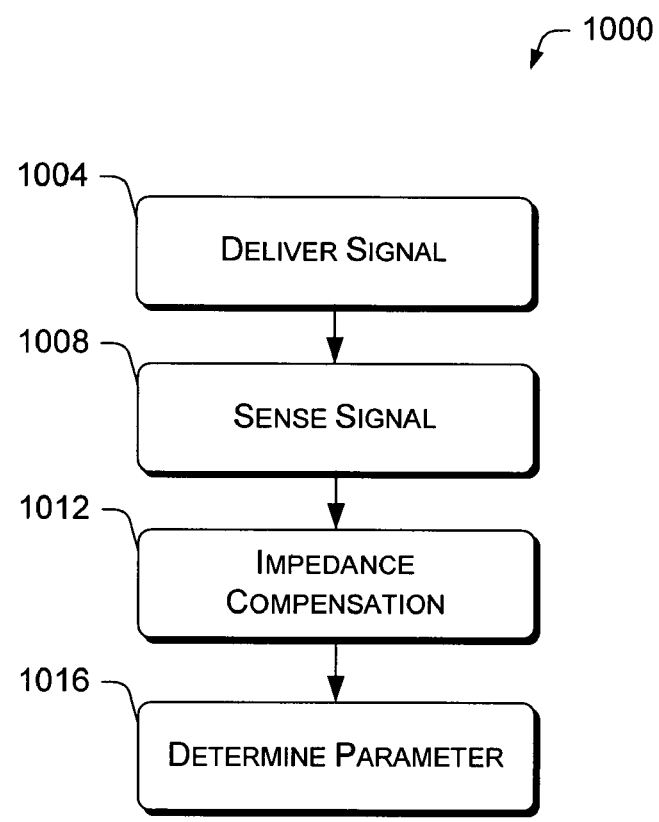
FIG. 10 is a block diagram of an exemplary method for compensating for impedance and determining a geometric parameter.

FIG. 10 shows an exemplary method 1000 for compensating for changes in impedance. According to the method 1000, a delivery block 1004 delivers an electrical signal to generate a potential field. At the same time, or shortly thereafter, a sense block 1008 senses a potential in the potential field. An impedance compensation block 1012 follows that compensates for changes in impedance, for example, changes that may effect a preexisting correlation between potential and geometry. A determination block 1016 follows the compensation block 1012 that determines a geometric parameter based, at least in part, on the potential and the impedance compensation.

The exemplary method 1000 may compensate for deviations in a potential field due to variability in tissue and body fluid. An exemplary arrangement, useful for unipolar signal delivery, includes delivering via a larger electrode (e.g., usually a ring or coil electrode) and sensing via a local voltage at the associated tip to determine impedance.

Another method for detecting or adjusting for an increased resistance or an impedance variation is simply to look at the classic impedance given from measured pacing data. For example, if a great deal of fibrosis exists near an electrode (e.g., RV-ring), it may lead to a resistance increase that should show in the measured data of pacing resistance, which uses the electrode in a bipolar configuration. Measurement of resistance for unipolar RV-ring pacing may also be available.

Pacing Therapy

Figure 11:
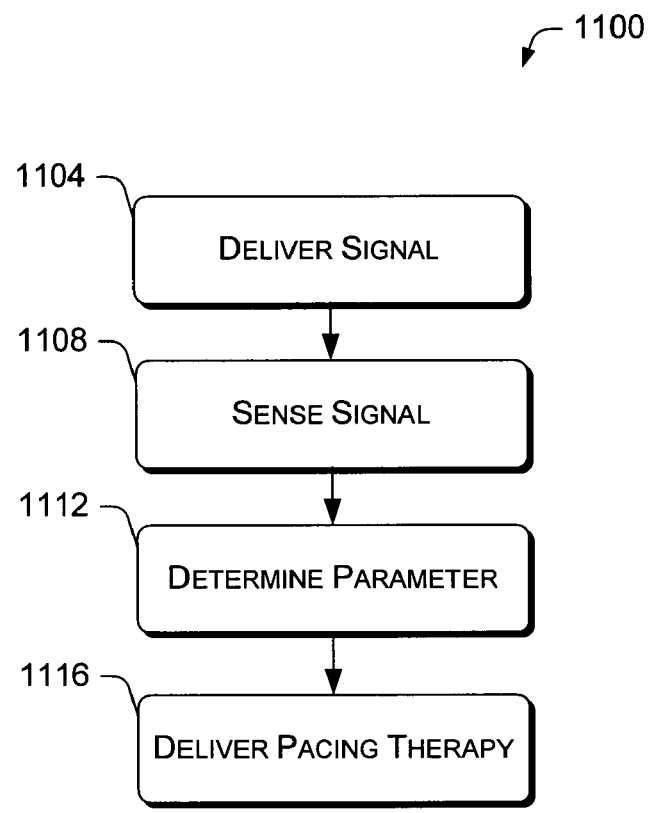
FIG. 11 is a block diagram of an exemplary method for determining a geometric parameter and delivering pacing therapy.

FIG. 11 shows an exemplary method 1100 for determining a geometric parameter. According to the method 1100, a delivery block 1104 delivers an electrical signal to generate a potential field. At the same time, or shortly thereafter, a sense block 1108 senses a potential in the potential field. A determination block 1112 follows that determines a geometric parameter based, at least in part, on the potential.

Various aforementioned exemplary methods, devices and/or systems are optionally used in combination to determine coordinates, for example, in a body defined coordinate system and/or an externally defined coordinate system.

CONCLUSION

Although various exemplary devices and/or methods have been described in language specific to structural features and/or methodological acts, it is to be understood that the subject matter defined in the appended claims is not necessarily limited to the specific features or acts described. Rather, the specific features and acts are disclosed as exemplary forms of implementing the claimed subject matter.

What is claimed is:

1. A method comprising:
   delivering an electrical signal to a first position using at least a first electrode located in or adjacent to a first cardiac chamber;
   sensing a potential generated by the delivered electrical signal using at least a second electrode located at a second position in or adjacent to a second cardiac chamber; and
   determining a change in an inter-electrode spacing between the first electrode and the second electrode based, at least in part, on a percent change of the sensed potential relative to a baseline potential.

2. The method of claim 1, wherein the delivering delivers the electrical signal using a unipolar configuration.

3. The method of claim 1, wherein the first position is in a right ventricle or in a vessel.

4. The method of claim 1, wherein the delivering delivers the electrical signal using a ring electrode.

5. The method of claim 1, Wherein the second position is in a vessel.

6. The method of claim 1, wherein the second position is in a cardiac chamber.

7. The method of claim 1, wherein the sensing senses the potential using a unipolar configuration.

8. The method of claim 1, wherein the sensing occurs during a refractory period.

9. The method of claim 1, wherein the delivering occurs during a refractory period.

10. The method of claim 1, further comprising determining a ventricular volume from the inter-electrode spacing between the first electrode and the second electrode.

11. The method of claim 1, further comprising determining a ventricular distance from the change in the inter-electrode spacing between the first electrode and the second electrode.

12. The method of claim 1, further comprising determining a left ventricular diameter from the change in the inter-electrode spacing between the first electrode and the second electrode.

13. The method of claim 1, further comprising determining a stage of congestive heart failure.

14. The method of claim 1, further comprising delivering cardiac therapy based, at least in part, on the sensing.

15. An apparatus comprising:
    means for delivering an electrical signal to a first position using at least a first electrode located in or adjacent to a first cardiac chamber;
    means for sensing a potential generated by the delivered electrical signal at a second position using at least a second electrode located in or adjacent to a second cardiac chamber;
    means for determining a percent change of the sensed potential relative to a baseline potential; and
    means for determining a change in an inter-electrode spacing between the first electrode and the second electrode based, at least in part, on the percent change of the sensed potential.

16. The apparatus of claim 15 wherein the means for delivering an electrical signal comprises a power source, a lead and an electrode.

17. The apparatus of claim 15 wherein the mean for sensing a potential comprises an electrode, a lead and a circuit.

18. The apparatus of claim 15 wherein the means for determining a change in an inter-electrode spacing comprises an implantable and programmable device.

19. An implantable cardiac system comprising:
    an implantable device having a case capable of acting as an electrode;
    one or more implantable leads having one or more electrodes wherein the one or more leads are connectable to the device; and
    circuitry that is operative to deliver an electrical signal to a first electrode position in or adjacent to a first cardiac chamber, sense a potential generated by the delivered electrical signal at a second electrode position in or adjacent to a second cardiac chamber, and
    a controller adapted to determine a percent change of the sensed potential relative to a baseline potential and to determine a change in an inter-electrode spacing between the first electrode and the second electrode based, at least in part, on the percent change of the sensed potential.

20. The system of claim 19 wherein the one or more implantable leads comprises at least two leads including a first lead that is configured for placement in a right ventricle and a second lead that is configured for placement in a left ventricle.

21. The system of claim 20 wherein the circuitry is operative to deliver an electrical signal to a first electrode carried by the first lead, and to sense a potential generated by the delivered electrical signal at a second electrode carried by the second lead.

22. A method comprising:
    delivering an electrical signal to a first position using a first electrode located in or adjacent to a cardiac chamber using a unipolar electrode configuration;
    sensing a potential generated by the delivered electrical signal using a second electrode located at a second position;
    determining a percent change of the sensed potential relative to a baseline potential; and
    determining a change in an inter-electrode spacing between the first electrode and the second electrode based, at least in part, on the percent change of the sensed potential.

* * * * *

UNITED STATES PATENT AND TRADEMARK OFFICE
CERTIFICATE OF CORRECTION

PATENT NO.        : 7,613,513 B1                                         Page 1 of 1
APPLICATION NO. : 10/612770
DATED             : November 3, 2009
INVENTOR(S)       : Brewer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1298 days.

Signed and Sealed this

Nineteenth Day of October, 2010

David J. Kappos
*Director of the United States Patent and Trademark Office*